(12) United States Patent
Hu et al.

(10) Patent No.: US 9,408,796 B2
(45) Date of Patent: Aug. 9, 2016

(54) COSMETIC COMPOSITIONS FOR IMPROVING THE APPEARANCE OF SKIN

(71) Applicant: Avon Products, Inc., New York, NY (US)

(72) Inventors: Hong Hu, Basking Ridge, NJ (US); Sunghan Yim, Lincoln Park, NJ (US); Uma Santhanam, Tenafly, NJ (US); John W. Lyga, Basking Ridge, NJ (US)

(73) Assignee: Avon Products, Inc, New York, NY (US)

( * ) Notice: Subject to any disclaimer, the term of this patent is extended or adjusted under 35 U.S.C. 154(b) by 0 days.

(21) Appl. No.: 14/409,506

(22) PCT Filed: Mar. 6, 2014

(86) PCT No.: PCT/US2014/021014
§ 371 (c)(1),
(2) Date: Dec. 19, 2014

(87) PCT Pub. No.: WO2014/158942
PCT Pub. Date: Oct. 2, 2014

(65) Prior Publication Data
US 2015/0190324 A1 Jul. 9, 2015

Related U.S. Application Data

(60) Provisional application No. 61/779,617, filed on Mar. 13, 2013.

(51) Int. Cl.
*A61K 8/49* (2006.01)
*A61Q 19/00* (2006.01)
*A61K 31/426* (2006.01)
*A61Q 19/08* (2006.01)
*C07D 277/30* (2006.01)
*A61K 8/06* (2006.01)
*A61K 8/36* (2006.01)
*A61Q 17/00* (2006.01)
*A61Q 19/02* (2006.01)

(52) U.S. Cl.
CPC ... *A61K 8/49* (2013.01); *A61K 8/06* (2013.01); *A61K 8/062* (2013.01); *A61K 8/064* (2013.01); *A61K 8/361* (2013.01); *A61K 31/426* (2013.01); *A61Q 17/00* (2013.01); *A61Q 19/02* (2013.01); *A61Q 19/08* (2013.01); *C07D 277/30* (2013.01); *A61K 2800/43* (2013.01); *A61K 2800/48* (2013.01); *A61K 2800/522* (2013.01); *A61K 2800/54* (2013.01)

(58) Field of Classification Search
CPC ................................. A61K 8/49; A61Q 19/00
See application file for complete search history.

(56) References Cited

U.S. PATENT DOCUMENTS

| | | | |
|---|---|---|---|
| 5,770,222 A | 6/1998 | Unger et al. | |
| 7,700,076 B2 | 4/2010 | Tamarkin et al. | |
| 8,920,785 B2 | 12/2014 | Kolbe et al. | |
| 9,289,364 B2 * | 3/2016 | Hu | A61K 8/494 |
| 2002/0128268 A1 | 9/2002 | Ley | |
| 2011/0112073 A1 | 5/2011 | Thiele et al. | |
| 2012/0022085 A1 | 1/2012 | Junior et al. | |

FOREIGN PATENT DOCUMENTS

| | | |
|---|---|---|
| EP | 1130017 B1 | 6/2005 |
| KR | 1020110097701 | 8/2011 |
| WO | 2008084962 A1 | 7/2008 |

OTHER PUBLICATIONS

Thanigaimalai et al., "Structure-activity relationship of naphthaldehydethiosemicarbazones in melanogenesis inhibition," Bioorganic & Medicinal Chemistry Letters, vol. 22, pp. 886-889 (2012).

Gao, Xing-Hua et al., "Efficacy and safety of innovative cosmeceuticals," Clinics in Dermatology, vol. 26, pp. 367-374 (2008).

Parvez, Shoukat et al., "Naurally Occurring Tyrosinase Inhibitors: Mechanism and Applications in Skin Health, cosmetics and Agriculture Industries," Phytotherapy Research, vol. 21, pp. 805-816 (2007).

Commonwealth of Pennsylvania. The Controlled Substances, Drugs, Devices and Cosmetic Act. Act of 1972, P.L. 233, No. 64, pp. 1-32 [online], [retrieved on May 6, 2014]. Retrieved from the Internet <URL: http://www.health.state.pa.us/pd/ddc/ddcAct.pdf>; p. 3, paragraph 16; p. 4, paragraph 12.

Pouillot, A. et al., Natural Antioxidants and their Effects on the Skin. Formulating, Packaging, and Marketing of Natural Cosmetic Products, First Edition, 2011, John Wiley & Sons, Inc. pp. 239-257 [online], [retrieved on May 6, 2014]; p. 241, paragraphs 2, 4 Retrieved from the internet <URL: http://www.alchimie-forever.com/img/wysiwyg/pdf/Chapter%2013%20natural@20antioxidants.pdf>.

* cited by examiner

*Primary Examiner* — Golam M Shameem
(74) *Attorney, Agent, or Firm* — David M. Joyal

(57) ABSTRACT

The present invention describes methods for improving the appearance of skin, particularly, treating, ameliorating, preventing, delaying, and/or improving one or more signs of aging, by topically applying compositions comprising arylthiazole compounds.

20 Claims, No Drawings

COSMETIC COMPOSITIONS FOR IMPROVING THE APPEARANCE OF SKIN

CROSS-REFERENCE TO RELATED APPLICATIONS

This application is a U.S. National Phase application of International Application No. PCT/US2014/021014, filed Mar. 6, 2014, which claims priority to U.S. Patent Application Ser. No. 61/779,617, filed on Mar. 13, 2013. The entirety of each application is incorporated by reference herein in its entirety. The International Application was published in English on Oct. 2, 2014 as Publication No. WO2014/158942.

FIELD OF INVENTION

The present invention relates generally to compositions for topical application to human integuments. In particular, the compositions of the present invention comprise aryl-thiazole compounds for providing aesthetic and therapeutic benefits to the skin, in particular, by improving the condition and appearance of skin affected by signs of chronological, hormonal, or photo-aging.

BACKGROUND OF THE INVENTION

Consumers constantly seek to improve the appearance of their skin, and in particular seek to improve the appearance of skin by reducing signs of skin aging, such as wrinkles and the like. Cosmetic products that enhance the appearance of skin are increasingly in demand as consumers increasingly seek to mitigate or forestall signs of aging, in particular of wrinkles and/or fine lines. In particular, there is an interest in products for cosmetic and therapeutic use on the skin.

Retinol is one of the most ubiquitous skin care active ingredients because of its ability to stimulate collagen synthesis. Enhancing collagen in the skin leads to improvements in the appearance of wrinkles, fine lines, and other attributes of the skin. However, the side effects of retinol are well-documented and may include irritation, excessive drying, and erythema.

It is therefore an object of the invention to provide new compositions and methods for combating signs of skin aging. It is another object of the invention to provide new compositions and methods for combating signs of skin aging which have improved side effect profiles (e.g., less irritating) compared to retinol. It is a further object of the invention to provide such compositions and methods to improve the overall appearance of skin, including treating, remediating, reversing, slowing, and/or preventing signs of aging, including signs of aging associated with degradation of collagen and/or elastin matrices and to enhance the regulation of new skin cells.

SUMMARY OF THE INVENTION

In accordance with the foregoing objectives and others, the present invention provides compositions comprising aryl-thiazole compounds for topical application to the skin. The inventive compounds can improve the overall appearance of skin, and in particular, one or more signs of dermatological aging, most notably improvement in the appearance of wrinkles and/or fine lines, including the reversal of wrinkles and fine lines that have already formed.

In one aspect of the invention, cosmetic compositions are provided for improving the aesthetic appearance of human skin comprising a cosmetically acceptable vehicle, and an effective amount of a compound according to formula I(a):

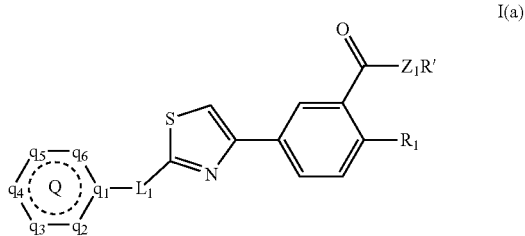

I(a)

wherein, $Z_1$ is O or N(R"); and $R_1$ is hydrogen or a group R; $L_1$ is absent or is a radical of the form $-X^a-(CH_2)_n-(CH=CH)_m-X^b-(CH_2)_n-(CH=CH)_m-X^c-$, where $X^a$, $X^b$, and $X^c$ are independently a bond (i.e., absent), $-O-$, $-S-$, $-NH-$, $-NR^*-$ and "n" and "m" are independently at each occurrence integers from 0-2, with the proviso that $L_1$ comprises no more than four atoms in the direct chain between the thiazole ring and Q;

wherein, $q_1$ is N or C and is the point of attachment to $L_1$, and $q_2$-$q_6$ are independently selected from $-N-$, $-NH-$, $-NR^*-$, $-O-$, $-S-$, $-CH-$, $-CR-$, $-CR^*-$, and in the case where ring Q is a five membered ring, one of $q_2$-$q_6$ is a bond (i.e., it is absent), and where the dashed circle in ring Q indicates that the ring is aromatic, partially unsaturated, or saturated;

R is selected from hydrogen, $-F$; $-Cl$; $-Br$; $-I$; $-OH$, $-OR^*$; $-NH_2$; $-NHR^*$; $-N(R^*)_2$; $-N(R^*)_3^+$; $-N(R^*)-OH$; $-N(\rightarrow O)(R^*)_2$; $-O-N(R^*)_2$; $-N(R^*)-O-R^*$; $-N(R^*)-N(R^*)_2$; $-C=N-R^*-$; $-N=C(R^*)_2$; $-C=N(R^*)_2$; $-C(=NR^*)-N(R^*)_2$; $-SH$; $-SR^*$; $-CN$; $-NC$; $-(C=O)-R^*$; $-CHO$; $-CO_2H$; $-CO_2^-$; $-CO_2R^*$; $-(C=O)-S-R^*$; $-O-(C=O)-H$; $-O-(C=O)-R^*$; $-S-(C=O)-R^*$; $-(C=O)-NH_2$; $-(C=O)-N(R^*)_2$; $-(C=O)-NHNH_2$; $-O-(C=O)-NHNH_2$; $-(C=S)-NH_2$; $-(C=S)-N(R^*)_2$; $-N(R^*)-CHO$; $-N(R^*)-(C=O)-R^*$; $-(C=NR)-O-R^*$; $-O-(C=NR^*)-R^*$, $-SCN$; $-NCS$; $-NSO$; $-SSR^*$; $-N(R^*)-C(=O)-N(R^*)_2$; $-N(R^*)-C(=S)-N(R^*)_2$; $-SO_2-R^*$; $-O-S(=O)_2-R^*$; $-S(=O)_2-OR^*$; $-N(R^*)-SO_2-R^*$; $-SO_2-N(R^*)_2$; $-O-SO_3^-$; $-O-S(=O)_2-OR^*$; $-O-S(=O)-OR^*$; $-O-S(=O)-R^*$; $-S(=O)-OR^*$; $-S(=O)-R^*$; $-NO$; $-NO_2$; $-NO_3$; $-O-NO$; $-O-NO_2$; $-N_3$; $-N_2-R^*$; $-N(C_2H_4)$; $-Si(R^*)_3$; $-CF_3$; $-O-CF_3$; $-PR^*_2$; $-O-P(=O)(OR^*)_2$; $-P(=O)(OR^*)_2$; $C_1$-$C_8$ perfluoroalkyl; an aliphatic $C_1$-$C_8$ hydrocarbon radical; a $C_1$-$C_8$ aromatic hydrocarbon radical; or a $C_1$-$C_8$ heteroaryl radical;

R* is independently at each occurrence hydrogen or a straight chained, branched, or cyclic $C_1$-$C_{10}$ hydrocarbon radical, which may be saturated, partially saturated, or aromatic, each of which may be optionally substituted with one or more groups R, or optionally substituted with 1-6 (e.g., 1-4 or 1-3) heteroatoms selected from nitrogen, oxygen, sulfur, or halogen;

R' and R" are independently selected from hydrogen, methyl, ethyl, butyl, propyl, pentyl, and hexyl, each of which may be optionally substituted with one or more groups R, or optionally substituted with 1-6 (e.g., 1-4 or 1-3) heteroatoms selected from nitrogen, oxygen, sulfur, or halogen; and wherein R' and R" may together from a 3-6 (e.g., five or six) membered heterocycle;

and cosmetically acceptable salts of the compounds of Formula I(a).

In some embodiment, $Z_1$ is N(R") and R' and R" are independently selected from hydrogen, methyl, ethyl, butyl, propyl, pentyl, and hexyl, and wherein R' and R" may together from a 3-6 (e.g., five or six) membered heterocycle optionally substituted with 1-3 heteroatoms selected from nitrogen, oxygen, or sulfur. In some embodiments, R' and R" are each hydrogen.

In some implementations, $R_1$ is selected from hydrogen, halogen, hydroxyl, thiol, amino, alkylamino, dialkylamino, methyl, ethyl, methoxy, ethoxy. In one embodiment, $R_1$ is hydroxyl.

In some implementations $L_1$ is a bond (i.e., it is absent) and in other implementations $L_1$ is selected from —O—, —S—, —NR*—, —(CH$_2$)$_n$—, —(CH$_2$)$_n$—O—, —O—(CH$_2$)$_n$—, —O—(CH$_2$)$_n$—O—, —(CH=CH)$_n$—, —(CH=CH)$_n$—O—, —(CH$_2$)$_n$—, —(CH$_2$)$_n$—S—, —S—(CH$_2$)$_n$—, —(CH=CH)$_n$—, —(CH=CH)$_n$—S—, —S—(CH=CH)$_n$—, —S—(CH=CH)$_n$—O—, —S—(CH=CH)$_n$—S—, —O—(CH=CH)$_n$—S—, —(CH$_2$)$_n$—NR*—, —NR*—(CH$_2$)$_n$—, —NR*—(CH$_2$)$_n$—O—, —NR*—(CH$_2$)$_n$—NR*—, —(CH=CH)$_n$—NR*—, —NR*—(CH=CH)$_n$—O—, —O—(CH=CH)$_n$—NR*—, —NR*—(CH=CH)$_n$—NR*—, —NR*—(CH=CH)$_n$—S—, —S—(CH=CH)$_n$—NR*—, —NR*—(CH=CH)$_n$—S—, —S—(CH=CH)$_n$—NR*—, —(CH$_2$)$_n$—O—(CH$_2$)$_n$—, —(CH$_2$)$_n$—S—(CH$_2$)$_n$—, —(CH$_2$)$_n$—NR*—(CH$_2$)$_n$—, wherein "n" is independently at each occurrence an integer from 0-3. In one embodiment, $L_1$ is a divalent radical of the form —(CH$_2$)$_n$—NR*—, including, for example, a group —CH$_2$—NH—.

In some implementations, ring Q has the form:

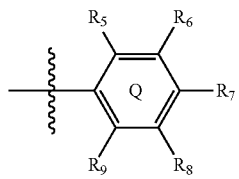

where $R_5$-$R_9$ are independently selected from hydrogen or R. In some implementations, at least one of $R_5$-$R_9$ is a group selected from hydroxyl, methoxy, ethoxy, amino, alkylamino, dialkylamino, thiol, thioether, cyano, methyl, ethyl, carboxyl, carbamyl, and nitro. In some embodiments, at least one of $R_5$-$R_9$ is methoxy or at least two of $R_5$-$R_9$ are methoxy. In one embodiment, $R_5$ is methoxy, in another embodiment, $R_5$ and $R_6$ are methoxy. In one embodiment, $R_5$ is methoxy and $R_6$-$R_9$ are hydrogen and in another embodiment, $R_5$ and $R_6$ are methoxy and $R_7$-$R_9$ are hydrogen.

In one implementation, the aryl-thiozole compound has the structure of Formula I(b):

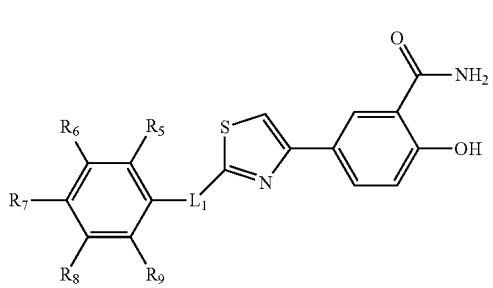

where $R_5$-$R_9$ are independently selected from hydrogen or R; and $L_1$ is a bond (i.e., it is absent) or a group —O—, —S—, —NR*—, —(CH$_2$)$_n$—, —(CH$_2$)$_n$—O—, —O—(CH$_2$)$_n$—, —O—(CH$_2$)$_n$—O—, —(CH=CH)$_n$—, —(CH=CH)$_n$—O—, —O—(CH=CH)$_n$—, —O—(CH=CH)$_n$—O—, —(CH$_2$)$_n$—(CH=CH)$_n$—, —(CH=CH)$_n$—(CH$_2$)$_n$—, —(CH$_2$)$_n$—S—, —S—(CH$_2$)$_n$—, —(CH=CH)$_n$—, —(CH=CH)$_n$—S—, —S—(CH=CH)$_n$—, —S—(CH=CH)$_n$—O—, —S—(CH=CH)$_n$—S—, —O—(CH=CH)$_n$—S—, —(CH$_2$)$_n$—NR*—, —NR*—(CH$_2$)$_n$—, —NR*—(CH$_2$)$_n$—O—, —NR*—(CH$_2$)$_n$—NR*—, —(CH=CH)$_n$—NR*—, —NR*—(CH=CH)$_n$—O—, —O—(CH=CH)$_n$—NR*—, —NR*—(CH=CH)$_n$—NR*—, —(CH$_2$)$_n$—NR*—, —NR*—(CH$_2$)$_n$—S—, —S—(CH$_2$)$_n$—NR*—, —NR*—(CH=CH)$_n$—S—, —S—(CH=CH)$_n$—NR*—, —(CH$_2$)$_n$—O—(CH$_2$)$_n$—, —(CH$_2$)$_n$—S—(CH$_2$)$_n$—, oe —(CH$_2$)$_n$—NR*—(CH$_2$)$_n$—, wherein "n" is independently at each occurrence an integer from 0-3.

In some embodiments, $L_1$ is a bond and in other embodiments, $L_1$ is —(CH$_2$)$_n$—NR*—, for example, $L_1$ may be —CH$_2$—NH—. In some embodiments $R_5$-R9 may each be hydrogen. In other embodiments, at least one of $R_5$-$R_9$ is a group selected from halo, hydroxyl, methoxy, ethoxy, amino, alkylamino, dialkylamino, thiol, thioether, cyano, methyl, ethyl, carboxyl, carbamyl, methyl, trifluoromethyl, and nitro, including embodiments where at least one of $R_5$-$R_9$ is a group selected from hydroxyl, methoxy, amino, alkylamino, dialkylamino, thiol, and thioether. In a particular embodiment, at least one of $R_5$-$R_9$ is methoxy. In another embodiment, at least two of $R_5$-$R_9$ are methoxy. In one embodiment, $R_5$ is methoxy and $R_6$-$R_9$ are hydrogen and in another embodiment, $R_5$ and $R_6$ are methoxy and $R_7$-$R_9$ are hydrogen.

In one implementation, the compound has the structure of Formula I(c):

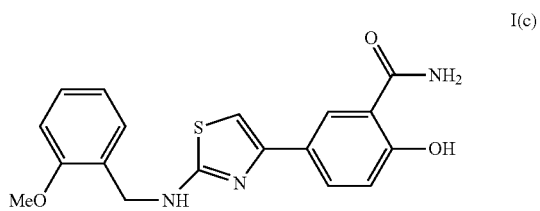 [SMILES: COc1ccccc1CNc1nc(-c2ccc(O)c(C(N)=O)c2)cs1]

and cosmetically acceptable salts thereof. In another implementation, the compound has the structure of Formula I(d):

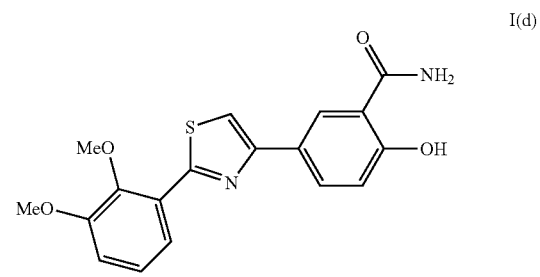 [SMILES: COc1cccc(-c2nc(-c3ccc(O)c(C(N)=O)c3)cs2)c1OC]

and cosmetically acceptable salts thereof.

The compositions of the invention may further comprise a cosmetic ingredient selected from a film forming polymer, a thickener, a pH adjuster, a preservative, an emulsifier, a gelling agent, an antioxidant, an emollient, a humectant, a fragrance, and a colorant. The composition may also comprise a cosmetically acceptable vehicle, such as a water-in-oil, oil-in-water, silicone-in-water, or water-in-silicone emulsion and further comprises an emulsifier. The aryl-thiazole compounds may be present in effective amounts which may be, for example, from about 0.00001% to about 1% by weight of said composition. The compositions may further comprise cosmetic auxiliaries and actives, and in particular a retinoid, including those selected from the group consisting of retinoic acid, retinol, retinal, retinyl acetate, and retinyl palmitate.

In one aspect of the invention, a method is provided for improving the aesthetic appearance of human skin comprising topically applying to an area of the skin in need thereof a composition comprising any of the aryl-thiazole compounds of the invention, for a time sufficient to improve the aesthetic appearance of said human skin. The aesthetic improvement of said human skin may include, without limitation:

(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and
(r) reduction of pigment spots and/or mottled skin; and
(s) improvement of optical properties of skin by light diffraction or reflection.

The compositions comprising the aryl-thiazole compounds are applied at least once daily (or twice daily) for a period of at least four weeks (or at least eight weeks, or at least twelve weeks, etc.).

In a related aspect, a method is provided for treating wrinkles and fine lines in human skin comprising topically applying to an affected area of the skin, a composition comprising any of the aryl-thiazole compounds of the invention, for a time sufficient to improve the appearance (e.g., reduce the depth or number) of the wrinkles and fine lines.

In another embodiment, a method is provided for treating thinning skin in a human (including males or females) comprising topically applying to an affected area of the skin a composition comprising any of the aryl-thiazole compounds of the invention, for a time sufficient to thicken said skin. The method is particular adapted to treating premature thinning in female skin, including thinning for which a clinical diagnosis has been made.

In another embodiment, a method is provided for treating sagging skin in a human comprising topically applying to an affected area of the skin a composition comprising any of the aryl-thiazole compounds of the invention, for a time sufficient to improve the elasticity of the skin.

In yet another embodiment, a method is provided for enhancing collagen in human skin comprising topically applying to an area of the skin in need thereof a composition comprising any of the aryl-thiazole compounds of the invention, for a time sufficient to enhance the production of collagen in the skin.

A method is also provided for enhancing hyaluronic acid in human skin comprising topically applying to an area of the skin in need thereof a composition comprising any of the aryl-thiazole compounds of the invention, for a time sufficient to enhance the production of hyaluronic acid said skin.

In another aspect, the invention relates to methods for improving the one or more signs of dermatological aging, such as wrinkles, comprising topically applying to the skin a cosmetic composition any of the aryl-thiazole compounds of the invention in a cosmetically acceptable vehicle in an amount effective to stimulate procollagen, collagen, and/or Hyaluronic Acid (HA) production in the skin. In a further embodiment, a method for increasing skin cell proliferation is provided, comprising topically applying to skin in need thereof an effective amount of any of the aryl-thiazole compounds of the invention.

Compositions and methods are also provided for improving the aesthetic appearance of human skin comprising topically applying to an area of the skin in need thereof a composition comprising any of the aryl-thiazole compounds of the invention, optionally in combination with an effective amount of a retinoid. In one embodiment, the retinoid is present in an amount below a level that induces irritation. In one embodiment, the aryl-thiazoles of the invention and retinoids will provide synergistic improvements in collagen production, hyaluronic acid production, and/or overall appearance of skin. The compositions typically will be formulated in a cosmetically acceptable vehicle, which will usually comprise an emulsion (e.g., water-in-oil or oil-in-water), stabilized with an emulsifier, and also may include other ingredients, such as skin actives (e.g., retinol, N-acetyl Tyrosinamide, etc.), antioxidants (e.g., TDPA), glycolic acid, preservatives, and the like. The compositions are topically applied to a human integument, such as the skin of the face, neck, lips, hands, chest, legs, scalp, etc., for a time sufficient to enhance the health or aesthetic appearance thereof, including reducing the number or severity of wrinkles and/or fine lines.

The composition will typically be applied to the skin one, two, or three times daily for as long as is necessary to achieve desired results. The treatment regiment may comprise daily application for at least one week, at least two weeks, at least four weeks, at least eight weeks, or at least twelve weeks or more. Chronic treatment regimens are also contemplated. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). In one embodiment, the composition of the invention will be applied to the skin in an amount from about 0.001 to about 100 mg/cm$^2$, more typically from about 0.01 to about 20 mg/cm$^2$, and preferably about 0.1 to about 10 mg/cm$^2$, in particular from about 1 to about 5 mg/cm$^2$, and ideally about 2 mg/cm$^2$.

These and other aspects of the present invention will be better understood by reference to the following detailed description.

DETAILED DESCRIPTION OF THE INVENTION

All terms used herein are intended to have their ordinary meaning unless otherwise provided. By "cosmetically acceptable," it is meant that a particular component is generally regarding as safe and non-toxic at the levels employed. The term "prevent," as used herein, includes delaying the onset of or progression of a particular sign of skin aging. The term "thin skin" includes skin that becomes thinner with chronological aging as well as prematurely thinned skin, which may be caused, for example, by photo-aging. In one embodiment, the prematurely thinned skin has been diagnosed as such by a clinician. In one embodiment, the prematurely thinned skin is female skin. In one embodiment, the prematurely thinned skin is male skin. In one embodiment, the thinned skin is female skin of a female that is postmenopausal. In one embodiment, the prematurely thinned skin is male skin.

The phrase "individual in need thereof" refers to a human that could benefit from improved dermal appearance or health, including males or females. In the preferred implementations of the invention, the compositions are applied to treat female skin. The individual in need thereof may be any age but will typically be a female aged 25-35 or 35-45 or 55-65 years old. The term "skin" includes, without limitation, the lips, skin of the face, hands, arms, neck, scalp, and chest. As used herein, the term "consisting essentially of" is intended to limit the invention to the specified materials or steps and those that do not materially affect the basic and novel characteristics of the claimed invention, as understood from a reading of this specification. As used herein, "% by weight" or "% wt" refers to the weight percent of a component in relation to the total weight of the composition or formulation (i.e., including any carriers, vehicles, solvents, emollients, fillers, or other components added before application to the skin) unless otherwise specified.

Without wishing to be bound by any particular theory, it is believed that the aryl-thiazole compounds of the present invention stimulate collagen and/or hyaluronic acid, thereby imparting an improved aesthetic appearance of skin, and reducing, preventing, or ameliorating unwanted characteristics, including but not limited to signs of chronological, hormonal, or photo-aging of human skin, such as wrinkles, fine lines, sagging skin, and thin skin, as well as other skin conditions, including hyperpigmentation (e.g., age spots and freckles). Also, without wishing to be bound by any particular theory, it is believed that the aryl-thiazoles of the invention have binding affinity for the retinol receptor. In one embodiment, the aryl-thiazoles of the invention have binding affinity for the retinol receptor. In one embodiment, the aryl-thiazoles of the invention have binding affinity for the retinol receptor comparable to the binding affinity of retinol. In one embodiment, the aryl-thiazoles of the invention have binding affinity for the retinol receptor superior to the binding affinity of retinol. However, unless otherwise specified, the invention is not limited to the use of aryl-thiazole compounds that bind the retinol receptor.

The aryl-thiazole compounds of the invention may be used in cosmetic preparations and may be formulated with other cosmetically acceptable components, and vehicles, e.g. emulsions or serums, into a composition for topical application to the skin. The compositions may include other ingredients, such as, for example, alkylene oxide copolymer, emulsifiers, sunscreens, thickeners, botanicals, film formers, pH adjusters, fragrances, and preservatives. The compositions are topically applied to the skin in effective amounts, by which is meant an amount sufficient to achieve a measurable improvement in skin health or reduction in one or more dermatological signs of aging with daily (once, twice, etc.) administration, typically for a period of at least one week or more. Such signs of skin aging include without limitation, the following:

(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and/or
(r) reduction of pigment spots and/or mottled skin
(s) improvement of optical properties of skin by light diffraction or reflection.

In practice, the compositions of the invention, comprising the aryl-thiazole compounds of the invention, in cosmetically acceptable vehicles, are applied to skin in need of treatment once or twice daily. That is, skin which suffers from a deficiency or loss in any of the foregoing attributes or which would otherwise benefit from improvement in any of the foregoing skin attributes. The treatment may continue for a week, two weeks, four weeks, eight weeks, six months or longer.

In one embodiment the active agents are topically applied, in a cosmetically acceptable vehicle, to skin suffering from fine lines and/or wrinkles to prevent, treat, and/or amelioration the appearance of the fine lines and/or wrinkles in the skin. In this case, the compositions are applied to skin in need of treatment, by which is meant skin already having wrinkles and/or fine lines or skin that is at risk of developing fine lines and/or wrinkles. Preferably, the compositions are applied directly to the fine lines and/or wrinkles on the skin of the face, neck, lips, chest, and/or hands. The compositions may remediate or reverse signs of aging by enhancing production of elastin, collagen, and procollagen in skin, by enhancing the extracellular matrix, or by improving cell proliferation. Typically, one or more additional skin actives will be included, such as retinol, TDPA, glycolic acid, N-acetyl Tyrosinamide, botanicals, and the like, for example, in amounts from about 0.0001% to about 5% by weight.

In one embodiment, the invention is directed to a method for improving the aesthetic appearance of human skin and/or improving the appearance of aged and/or photo-damaged skin by increasing the production of elastin, collagen, and procollagen in the skin, the method comprising topically applying to an area of the skin in need thereof an effective amount of any of the (e.g., collagen stimulating) aryl-thiazole compounds of the invention and a cosmetically acceptable vehicle.

In one aspect of the invention, cosmetic compositions are provided for improving the aesthetic appearance of human skin comprising a cosmetically acceptable vehicle, and an effective amount of a (e.g., collagen stimulating) compound according to formula I(a):

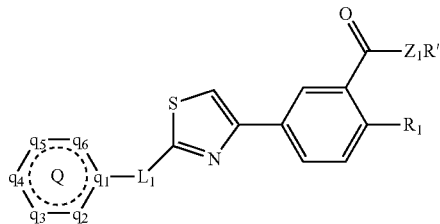

I(a)

wherein, $Z_1$ is O or N(R");

$R_1$ is hydrogen or a group R; and in some embodiments, $R_1$ is selected from hydrogen, halogen, hydroxyl, thiol, amino, alkylamino (e.g., methylamino or ethylamino), dialkylamino (e.g., dimethylamino or diethylamino), methyl, ethyl, methoxy, ethoxy. In some embodiments, $R_1$ is thiol. In some embodiments, $R_1$ is amino. In some embodiments, $R_1$ is hydroxyl.

$L_1$ is a bond (i.e., it is absent) or is a radical of the form $-X^a-(CH_2)_n-(CH=CH)_m-X^b-(CH_2)_n-(CH=CH)_m-X^c-$, where $X^a$, $X^b$, and $X^c$ are independently a bond (i.e., absent), $-O-$, $-S-$, $-NH-$, $-NR^*-$ and "n" and "m" are independently at each occurrence integers from 0-2, with the proviso that $L_1$ comprises no more than four atoms in the direct chain between the thiazole ring and Q;

In one embodiment, $L_1$ is a bond (i.e., it is absent) such that q1 is connected directly to the thiazole ring. In another embodiment, $L_1$ a group $-O-$, $-S-$, $-NR^*-$, $-(CH_2)_n-$, $-(CH_2)_n-O-$, $-O-(CH_2)_n-$, $-O-(CH_2)_n-O-$, $-(CH=CH)_n-$, $-(CH=CH)_n-O-$, $-O-(CH=CH)_n-$, $-O-(CH=CH)_n-O-$, $-(CH_2)_n-(CH=CH)_n-$, $-(CH=CH)_n-(CH_2)_n-$, $-(CH_2)_n-S-$, $-S-(CH_2)_n-$, $-(CH=CH)_n-$, $-(CH=CH)_n-S-$, $-S-(CH=CH)_n-$, $-S-(CH=CH)_n-O-$, $-S-(CH=CH)_n-S-$, $-O-(CH=CH)_n-S-$, $-(CH_2)_n-NR^*-$, $-NR^*-(CH_2)_n-$, $-NR^*-(CH_2)_n-O-$, $-NR^*-(CH_2)_n-NR^*-$, $-(CH=CH)_n-NR^*-$, $-NR^*-(CH=CH)_n-O-$, $-O-(CH=CH)_n-NR^*-$, $-NR^*-(CH=CH)_n-NR^*-$, $-NR^*-(CH_2)_n-S-$, $-S-(CH_2)_n-NR^*-$, $-NR^*-(CH=CH)_n-S-$, $-S-(CH=CH)_n-NR^*-$, $-(CH_2)_n-O-(CH_2)_n-$, $-(CH_2)_n-S-(CH_2)_n-$, oe $-(CH_2)_n-NR^*-(CH_2)_n-$, wherein "n" is independently at each occurrence an integer from 0-3.

In some embodiments, $L_1$ is a divalent radical of the form $-(CH_2)_n-NR^*-$ (where n is one, two, or three), and where $R^*$ is hydrogen or lower alkyl (e.g., methyl, ethyl, etc.), and for example, $L_1$ may be $-CH_2-NH-$.

Ring Q is a five or six membered optionally aromatic ring which opinion contain heteroatoms in the ring (e.g., Q is a heterocycle). In some embodiments, $q_1$ is N or C and is the point of attachment to $L_1$. In some embodiments, $q_2$-$q_6$ are independently selected from $-N-$, $-NH-$, $-NR^*-$, $-O-$, $-S-$, $-CH-$, $-CR-$, $-CR^*-$, and in the case where ring Q is a five membered ring, one of $q_2$-$q_6$ is a bond (i.e., it is absent), and where the dashed circle in ring Q indicates that the ring is aromatic, partially unsaturated, or saturated. In one embodiment, ring Q is aromatic, and for example, Q may have the form:

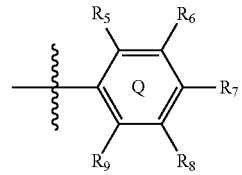

where $R_5$-$R_9$ are independently selected from hydrogen or R, where R is selected from hydrogen, $-F$; $-Cl$; $-Br$; $-I$; $-OH$, $-OR^*$; $-NH_2$; $-NHR^*$; $-N(R^*)_2$; $-N(R^*)_3^+$; $-N(R^*)-OH$; $-N(\rightarrow O)(R^*)_2$; $-O-N(R^*)_2$; $-N(R^*)-O-R^*$; $-N(R^*)-N(R^*)_2$; $-C=N-R^*$; $-N=C(R^*)_2$; $-C=N-N(R^*)_2$; $-C(=NR^*)-N(R^*)_2$; $-SH$; $-SR^*$; $-CN$; $-NC$; $-(C=O)-R^*$; $-CHO$; $-CO_2H$; $-CO_2^-$; $-CO_2R^*$; $-(C=O)-S-R^*$; $-O-(C=O)-H$; $-O-(C=O)-R^*$; $-S-(C=O)-R^*$; $-(C=O)-NH_2$; $-(C=O)-N(R^*)_2$; $-(C=O)-NHNH_2$; $-O-(C=O)-NHNH_2$; $-(C=S)-NH_2$; $-(C=S)-N(R^*)_2$; $-N(R^*)-CHO$; $-N(R^*)-(C=O)-R^*$; $-(C=NR)-O-R^*$; $-O-(C=NR^*)-R^*$, $-SCN$; $-NCS$; $-NSO$; $-SSR^*$; $-N(R^*)-C(=O)-N(R^*)_2$; $-N(R^*)-C(=S)-N(R^*)_2$; $-SO_2-R^*$; $-O-S(=O)_2-R^*$; $-S(=O)_2-OR^*$; $-N(R^*)-SO_2-R^*$; $-SO_2-SO_3^-$; $-O-S(=O)_2-OR^*$; $-O-S(=O)-OR^*$; $-O-S(=O)-R^*$; $-S(=O)-OR^*$; $-S(=O)-R^*$; $-NO$; $-NO_2$; $-NO_3$; $-O-NO$; $-O-NO_2$; $-N_3$; $-N_2-R^*$; $-N(C_2H_4)$; $-Si(R^*)_3$; $-CF_3$; $-O-CF_3$; $-PR^*_2$; $-O-P(=O)(OR^*)_2$; $-P(=O)(OR^*)_2$; $C_1$-$C_8$ perfluoroalkyl; an aliphatic $C_1$-$C_8$ hydrocarbon radical; a $C_1$-$C_8$ aromatic hydrocarbon radical; or a $C_1$-$C_8$ heteroaryl radical.

In one embodiment $R_5$ is hydrogen. In one embodiment $R_6$ is hydrogen. In one embodiment $R_7$ is hydrogen. In one embodiment $R_7$ is hydrogen. In one embodiment $R_8$ is hydrogen. In one embodiment $R_9$ is hydrogen. In some embodiments $R_5$-$R_9$ may each be hydrogen.

In other embodiments, at least one of $R_5$-$R_9$ is a group selected from halo, hydroxyl, methoxy, ethoxy, amino, alkylamino, dialkylamino, thiol, thioether, cyano, methyl, ethyl, carboxyl, carbamyl, methyl, trifluoromethyl, and nitro, including embodiments where at least one of $R_5$-$R_9$ is a group selected from hydroxyl, methoxy, amino, alkylamino, dialkylamino, thiol, and thioether. In a particular embodiment, at least one of $R_5$-$R_9$ is methoxy. In another embodiment, at least two of $R_5$-$R_9$ are methoxy. In one embodiment, $R_5$ is methoxy and $R_6$-$R_9$ are hydrogen and in another embodiment, $R_5$ and $R_6$ are methoxy and $R_7$-$R_9$ are hydrogen.

$R^*$ is independently at each occurrence hydrogen or a straight chained, branched, or cyclic $C_1$-$C_{10}$ or $C_1$-$C_8$ or $C_1$-$C_6$ or $C_1$-$C_4$ hydrocarbon radical, which may be saturated, partially saturated, or aromatic, each of which may be optionally substituted with one or more (e.g., one two, three, etc.) groups R, or optionally substituted with 1-6 (e.g., 1-4 or 1-3) heteroatoms selected from nitrogen, oxygen, sulfur, or halogen.

R' and R" are independently selected from hydrogen, methyl, ethyl, butyl, propyl, pentyl, and hexyl, each of which may be optionally substituted with one or more (e.g., one two, three, etc.) groups R, or optionally substituted with 1-6 (e.g., 1-4 or 1-3) heteroatoms selected from nitrogen, oxygen, sulfur, or halogen; and wherein R' and R" may together from a 3-6 membered heterocycle;

In some embodiments, $Z_1$ is N(R") and R' and R" are independently selected from hydrogen, methyl, ethyl, butyl, propyl, pentyl, and hexyl, and wherein R' and R" may together from a 3-6 membered heterocycle optionally substituted with 1-3 heteroatoms selected from nitrogen, oxygen, or sulfur. In some embodiments, one of R' and R" are hydrogen. In other embodiments, R' and R" are each hydrogen.

In other embodiments, Q represents a five-membered heterocyclic ring selected from the following:

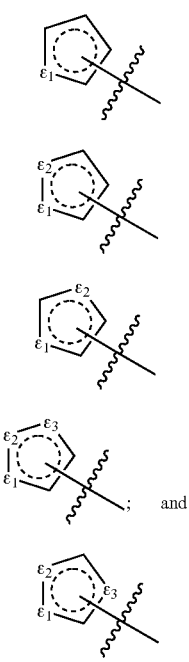

wherein $\epsilon_1$, $\epsilon_2$, and $\epsilon_3$, are independently selected from N, NH, NR*, S, and O; with the proviso that where the point of attachment is $\epsilon_1$, $\epsilon_2$, or $\epsilon_3$, then that position represents N; and wherein carbon atoms which are not the point of attachment may be optionally substituted with a group R; and wherein the dashed circles indicate that each ring may comprise zero, one, or two double bonds.

In one embodiment, the compound has the structure of Formula I(b):

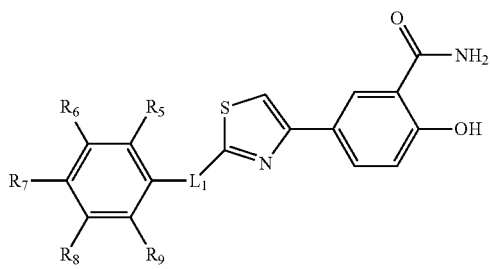

I(b)

where $R_5$-$R_9$ are independently selected from hydrogen or R (e.g., halo, hydroxyl, methoxy, ethoxy, amino, alkylamino, dialkylamino, thiol, thioether, cyano, methyl, ethyl, carboxyl, carbamyl, methyl, trifluoromethyl, nitro etc.); $L_1$ is a bond (i.e., it is absent) or a group as defined previously, or in particular a group —O—, —S—, —NR*—, —(CH$_2$)$_n$—, —(CH$_2$)$_n$—O—, —O—(CH$_2$)$_n$—, —O—(CH$_2$)$_n$—O—, —(CH=CH)$_n$—, —(CH=CH)$_n$—O—, —O—(CH= CH)$_n$—, —O—(CH=CH)$_n$—O—, —(CH$_2$)$_n$—(CH= CH)$_n$—, —(CH=CH)$_n$—(CH$_2$)$_n$—, —(CH$_2$)$_n$—S—, —S— (CH$_2$)$_n$—, —(CH=CH)$_n$—, —(CH=CH)$_n$—S—, —S— (CH=CH)$_n$—, —S—(CH=CH)$_n$—O—, —S—(CH= CH)$_n$—S—, —O—(CH=CH)$_n$—S—, —(CH$_2$)$_n$—NR*—, —NR*—(CH$_2$)$_n$—, —NR*—(CH$_2$)$_n$—O—, —NR*— (CH$_2$)$_n$—NR*—, —(CH=CH)$_n$—NR*—, —NR*— (CH=CH)$_n$—O—, —O—(CH=CH)$_n$—NR*—, —NR*— (CH=CH)$_n$—NR*—, —NR*—(CH$_2$)$_n$—S—, —S— (CH$_2$)$_n$—NR*—, —NR*—(CH=CH)$_n$—S—, —S— (CH=CH)$_n$—NR*—, —(CH$_2$)$_n$—O—(CH$_2$)$_n$—, —(CH$_2$)$_n$—S—(CH$_2$)$_n$—, —(CH$_2$)$_n$—NR*—(CH$_2$)$_n$—, wherein "n" is independently at each occurrence an integer from 0-3.

In one embodiment according to Formula I(b), $L_1$ is a bond. In another embodiment according to Formula I(b), $L_1$ is —(CH$_2$)$_n$—NR*—. In another embodiment according to Formula I(b), $L_1$ is —CH$_2$—NH—. In a particular embodiment according to Formula I(b), at least one of $R_5$-$R_9$ is methoxy. In another embodiment, at least two of $R_5$-$R_9$ are methoxy. In one embodiment, $R_5$ is methoxy and $R_6$-$R_9$ are hydrogen and in another embodiment, $R_5$ and $R_6$ are methoxy and $R_7$-$R_9$ are hydrogen.

In one embodiment, the compound has the structure of Formula I(c):

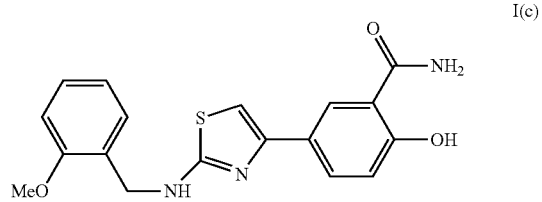 [SMILES: COc1ccccc1CNc1nc(-c2ccc(O)c(C(N)=O)c2)cs1]

I(c)

and cosmetically acceptable salts thereof.

In another embodiment, the compound has the structure of Formula I(d):

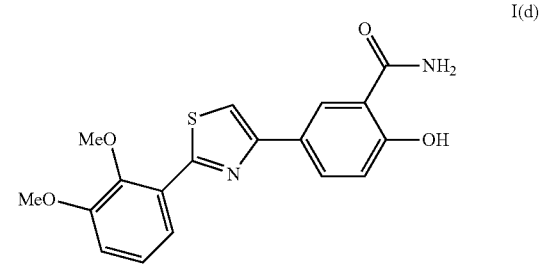 [SMILES: COc1cccc(-c2nc(-c3ccc(O)c(C(N)=O)c3)cs2)c1OC]

I(d)

and cosmetically acceptable salts thereof.

In some embodiments, the aryl-thiazole compounds of the invention further comprise a cosmetic ingredient selected from a film forming polymer, a thickener, a pH adjuster, a preservative, an emulsifier, a gelling agent, an antioxidant, an emollient, a humectant, a fragrance, and a colorant. In some embodiments, the compositions further comprise a cosmetically acceptable vehicle comprises a water-in-oil, oil-in-water, silicone-in-water, or water-in-silicone emulsion and further comprises an emulsifier.

The cosmetic composition may comprise an effective amount of any of the aryl-thiazole compounds of the invention, which may be, for example, from about 0.00001% to about 5% by weight of the composition, or from about 0.0001% to about 2.5% by weight of said composition, or from about 0.001% to about 1.5% by weight of the composition, or from about 0.01% to about 1% by weight of the composition.

The compositions can include a cosmetically acceptable vehicle. Such vehicles may take the form of any known vehicle in the art suitable for application to skin and may include, but are not limited to, water; vegetable oils; mineral oils; esters such as octal palmitate, isopropyl myristate, myristyl myristate, and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as dimethicone and cyclomethicone, hydrocarbon oils such as mineral oil, petrolatum, isoeicosane and (hydrogenated) polyisobutene; polyols such as propylene glycol, glycerin, butylene glycol, pentylene glycol, hexylene glycol, and caprylyl glycol; liposomes; waxes; or any combinations or mixtures of the foregoing.

The vehicle may comprise an aqueous phase, an oil phase, a glycerin phase, an alcohol, a silicone phase or mixtures thereof and may be in the form of an emulsion. Non-limiting examples of suitable emulsions include water-in-oil emulsions, oil-in-water emulsions, silicone-in-water emulsions, water-in-silicone emulsions, glycerin-in-oil emulsions, wax-in-water emulsions, water-oil-water triple emulsions or the like. The emulsion may include an emulsifier, such as a nonionic, anionic or amphoteric surfactant, or a gelling agent.

In one embodiment of the invention, the compositions may include additional skin actives, including but not limited to, retinoids (e.g., retinol, and the like), botanicals, keratolytic agents, desquamating agents, keratinocyte proliferation enhancers, collagenase inhibitors, elastase inhibitors, depigmenting agents, anti-inflammatory agents, steroids, anti-acne agents (e.g., salicylic acid, triclosan, and the like), antioxidants, desthiobiotin, piperazine carboxamide, $C_{12-15}$ alkyl benzoate, cis-6-nonenol, caffeine, arginine, glucosamine, algae extract, chlorphenesin, advanced glycation end-product (AGE) inhibitors, PLOD-2 stimulators (e.g., N-acetyl amino acid amides, such as N-Acetyl Tyrosinamide).

The compositions may comprise additional active ingredients having anti-aging benefits, as it is contemplated that synergistic improvements may be obtained with such combinations. Exemplary anti-aging components include, without limitation, botanicals (e.g., *Butea frondosa* extract); phytol; thiodipropionic acid (TDPA) and esters thereof; retinoids (e.g., 9-cis retinoic acid, 13-cis retinoic acid, all-trans retinoic acid, derivatives thereof, and salts thereof, phytanic acid, retinol (Vitamin A) and esters thereof, such as retinol palmitate, retinol acetate and retinol propionate, and others); hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few.

In some embodiments, the cosmetic compositions can further comprise at least one additional collagen and/or elastin stimulator. Such collagen or elastin stimulators are effective in, for example, providing improvement in procollagen and/or collagen production and/or improvement in maintenance and remodeling of elastin. A compound or substance is determined to be a collagen and/or elastin upregulator by, for example, assaying keratinocytes and/or fibroblasts of the skin and determining whether the candidate substance upregulates cellular mRNA encoding collagen and/or elastin.

In some embodiments, the topical formulations may also include one or more antioxidants. An antioxidant functions, among other things, to scavenge free radicals from skin, protecting the skin from environmental aggressors. Examples of antioxidants that may be used in the present compositions and formulations include compounds having phenolic hydroxy functions, such as ascorbic acid and its derivatives/esters; thiodipropionic acid and its esters; vitamins A, C, or E; polyphenols, beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may have an antioxidant preferably from about 0.001 weight % to about 10 weight %, and more preferably from about 0.01 weight % to about 5 weight %, based on the total weight of the composition or formulation.

In some embodiments, formulations may have one or more retinoids. Exemplary retinoids include, without limitation, retinoic acid (e.g., all-trans or 13-cis), derivatives thereof, and salts thereof, retinaldehyde, retinol (Vitamin A) and esters thereof, such as retinyl palmitate, retinyl acetate and retinyl propionate. Retinoids may comprise from about 0.001 weight % to about 10 weight %, and more typically from about 0.01 weight % to about 5 weight %, based on the total weight of the composition or formulation.

In some embodiments, formulations may have one or more exfoliation promoters. Suitable examples of exfoliation promoters include alpha hydroxy acids (AHA); benzoyl peroxide; beta hydroxy acids; keto acids, such as pyruvic acid, 2-oxopropanoic acid, 2-oxobutanoic acid, and 2-oxopentanoic acid; oxa acids as disclosed in U.S. Pat. Nos. 5,847,003 and 5,834,513 (the disclosures of which are incorporated herein by reference); salicylic acid; urea; or any mixtures thereof. The preferred exfoliation promoters are 3,6,9-trioxaundecanedioic acid, glycolic acid, lactic acid, or any mixtures thereof. When an embodiment of the invention includes an exfoliation promoter, the formulation may have from about 0.1 weight % to about 30 weight %, preferably from about 1 weight % to about 15 weight %, and more preferably from about 1 weight % to about 10 weight %, of the exfoliation promoter based on the total weight of the composition or formulation.

The compositions comprising the aryl-thiazole compounds of the invention may further comprise a retinoid. Suitable retinoids may, for example, be selected from the group consisting of retinoic acid, retinol, retinal, retinyl acetate, and retinyl palmitate. The compositions comprising the aryl-thiazole compounds of the invention may further comprise N-Acetyl Tyrosinamide. The compositions comprising the aryl-thiazole compounds of the invention may further comprise glycolic acid. Retinoids, N-Acetyl Tyrosinamide, and/or glycolic acid may individually or collectively be present in amounts from about 0.00001% to about 5% by weight of the composition, or from about 0.0001% to about 2.5% by weight of said composition, or from about 0.001% to about 1.5% by weight of the composition, or from about 0.01% to about 1% by weight of the composition.

In some embodiments, the compositions may comprise one or more botanicals. Suitable botanicals include, without limitation, *Abies pindrow, Abrus fruticulosus, Acacia catechu, Acacia melanoxylon, Alisma orientale, Amorphophallus campanulatus, Anogeissus latifolia, Archidendron clypearia, Asmunda japonica, Averrhoa carambola, Azadirachta indica, Berchemia lineate, Breynia fruticosa, Butea frondosa, Butea monosperma, Caesalpinia sappan Linn, Calatropis gigantean, Cayratia japonica, Cedrus deodara, Celosia argentea, Cistanche tubulosa, Clerodendron fragrans, Clerodendrum floribundum, Clinacanthus nutans, cola, Commersonia bartramia, Dendranthema indicum, Derris scandens, Desmanthus illinoensis, Dianella ensifolia, Dodonaea viscose, Duboisa myoporoides, Eclipta prostrate, Ehretia acuminate, Emblica officinalis, Erthrina Flabelliformis, Erythina indica, Fibraretinum resica Pierre, Ficus benghalensis, Ficus coronata, forskohlii, Ginkgo biloba, Glycyrrhiza glabra, Gomphrena globosa Linn, Goodenia ovata, Gynandropsis gynandra, hawthorne, Helichrysum Odoratissimum, Heliotropium indicum, Humulus japonicus, Hymenosporum flavum, Ilex purpurea Hassk, Innula racemosa, Ixora chinensis, Justicia ventricosa, Lavatera plebeian, Ligusticum chiangxiong, Ligusticum lucidum, Loropetalum chinense, Maesa japonica, Mallotus philippinensis, Mammea siamensis, Medemia nobilis, Melaleuca quinquernervia, Melicope hayesii, Mimusops elengi, Morinda citrifolia, Moringa oleifera, Naringi crenulata, Nerium indicum, Omolanthes populifolius, Operculina turpethum, Orthosiphon grandiflorus, Ozothamnus Obcordatus, Physalis minima, Portulaca oleracea, Pouzolzia pentandra, Psoralea corylifolia, Pteris semipinnata, Raphia farinifera, Sambucus chinensis, Sapindus rarak, Scoparis dulcis, Sesbania grandiflora, Stenoloma chusana, Tagetes erecta Linn, Terminalia bellerica, Tiliacora triandra,* tomato glycolipid, *Vernonia cinerea* Linn. Less, yohimbine, aloe, chamomile, and combinations thereof.

In another embodiment, the topical compositions of the present invention may also include one or more of the following: an emollient, a skin plumper, a skin penetration enhancer, a humectant (such as glycerin or caprylyl glycol), a sunscreen (e.g., avobenzone, octylmethoxy cinnamate, octyl salicylate, oxybenzone, titanium dioxide, zinc oxide, or any mixtures thereof), an exfoliating agent, and/or an antioxidant. When present, these components will comprise from about 0.1% to about 20% by weight of the composition.

An emollient provides the functional benefits of enhancing skin smoothness and may aid in improving the appearance of skin affected by aging. Examples of emollients include isopropyl myristate, petrolatum, isopropyl lanolate, silicones (e.g., methicone, dimethicone), oils, mineral oils, fatty acid esters, or any mixtures thereof. The emollient is preferably present from about 0.1 wt % to about 50 wt % of the total weight of the composition or formulation.

A skin plumper serves as a collagen enhancer to the skin. An example of a suitable, and preferred, skin plumper is palmitoyl oligopeptide. Other skin plumpers are collagen and/or glycosaminoglycan (GAG) enhancing agents. The skin plumper is preferably present from about 0.1 weight % to about 20 weight % of the total weight of the composition or formulation.

The formulations for use in the inventive methods may further comprise any ingredient conventionally used in the cosmetics field. These ingredients include, e.g., preserving agents, aqueous phase thickeners (polysaccharide biopolymers, synthetic polymers), fatty-phase thickeners, fragrances, hydrophilic and lipophilic active agents, and mixtures thereof. The amounts of these various ingredients are those conventionally used in the cosmetics field to achieve their intended purpose, and range typically from about 0.01 weight % to about 20 weight %, based upon the total weight of the composition or formulation. The nature of these ingredients and their amounts will be selected to be compatible with the production and intended applications of the compositions, as described herein.

In some embodiments, the formulation may also have one or more of the following cosmetic and pharmaceutical active agents, excipients, ingredients, or adjuvants: anesthetics; antibiotics; salicylic acids; anti-allergenics; antifungals; antiseptics; anti-irritants; anti-inflammatory agents; antimicrobials; analgesics; nitric oxide synthase inhibitors; insect repellents; self-tanning agents; skin penetration enhancers; skin cooling agents; chelating agents; colorants including dyes, lakes and pigments that may be untreated or chemically surface treated to improve wetability or some other property; demulcents; emulsifiers; fragrances; humectants; lubricants; skin protectants; moisturizers; pH adjusters; preservatives; stabilizers; surfactants; thickeners; film formers; plasticizers; viscosity modifiers; vitamins; blood flow stimulators; or any mixtures thereof. The amounts of these various substances are those that are conventionally used in the cosmetic or pharmaceutical fields to achieve their intended purposes, for example, they may constitute from about 0.01 weight % to about 20 weight % of the total weight of the composition or formulation.

In some embodiments, the cosmetic composition further comprises at least one cosmetically acceptable preservative. Exemplary preservatives include, without limitation, EDTA, disodium EDTA, phenoxyethanol, methyl paraben, ethyl paraben, propyl paraben, imidazolidinyl urea, sodium dehydroacetate, para-hydroxybenzoic acid, hydantoin derivatives, propionate salts, quaternary ammonium compounds, benzyl alcohol, caprylyl glycol, butylated hydroxytoluene (BHT), and combinations thereof.

In some embodiments, the formulation may optionally comprise a particulate phase, typically present in an amount of from about 0.01 weight % to about 30 weight %, based upon the total weight of the composition or formulation, preferably from about 0.1 weight % to about 20 weight %, and which can comprise pigments and/or pearlescent agents and/or fillers and/or polymeric particulates and beads used in cosmetic compositions.

The general activity and mildness to skin of compositions according to the invention can also be enhanced by neutralization to a pH from about 2 to about 8, with a pH in the range of from 3 to 7 being preferred. In some embodiment, the composition will have a pH in the range of from 3.5 to 5.5. Suitable pH adjusters is accomplished using one or more of adjusters, such as ammonium chloride, ammonium hydroxide, potassium hydroxide, sodium hydroxide, arginine or other amino acids, citric acid, hydrochloric acid, lactic acid, and/or triethanolamine, to bring the pH within the desired range.

In accordance with the invention, the aryl-thiazole compounds of the invention may be formulated in a variety of product forms, such as, for example, an emulsion, lotion, cream, serum, spray, aerosol, cake, ointment, essence, gel, paste, patch, pencil, towelette, mask, stick, foam, elixir, concentrate, and the like, particularly for topical administration. Preferably the composition is formulated as an emulsion, lotion, cream, ointment, serum or gel.

In yet other embodiments, the compositions are formulated into liposomes or microspheres, which can comprise other additives or substances, and/or which can be modified to more specifically target or remain at a site following administration. (See, e.g., U.S. Pat. No. 5,770,222 to Unger et al., incorporated herein by reference.).

Another aspect of the instant invention relates to cosmetic use of compositions comprising any of the aryl-thiazole compounds of the invention. The compounds are believed to remediate, reverse, reduce, ameliorate, forestall, or prevent dermatological signs of aging, as well as to improve the aesthetic appearance of skin.

Generally, the improvement in the condition and/or aesthetic appearance is selected from the group consisting of: reducing dermatological signs of chronological aging, photoaging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation or hypopigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; slowing or halting skin thinning; increasing skin elasticity and/or resiliency; enhancing exfoliation; improving microcirculation; decreasing and/or preventing cellulite formation; and any combinations thereof.

"Treatment" as used herein, as well as related terms such as "treat" or "treating," refers to eradicating, reducing, ameliorating, or reversing one or more of the unwanted features associated with the skin condition being treated, such that the consumer or clinician perceives an improvement in the appearance of the skin or other treatment benefit with respect to the condition. "Prevention" as used herein, as well as related terms such as "prevent" or "preventing," refers to affording skin not yet affected by the condition a benefit that serves to avoid, delay, forestall, minimize, or reduce the recurrence one or more unwanted features associated with the skin condition to be prevented. Such preventative benefits include, for example, delaying development and/or recurrence of the condition, or reducing the duration, severity, or intensity of one or more unwanted features associated with the condition if it eventually develops.

In some embodiments, the compounds of Formulas I(a)-I(d) will be used to reduce the severity of fine lines or wrinkles, often in combination with retinol. The composition will typically be applied to the skin one, two, or three times daily for as long as is necessary to achieve desired results. The treatment regimen may comprise daily application for at least one week, at least two weeks, at least four weeks, at least eight weeks, or at least twelve weeks or more. Chronic treatment regimens are also contemplated. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). In one embodiment, the cosmetic compositions of the invention will be applied to the skin in an amount from about 0.001 to about 100 mg/cm$^2$, more typically from about 0.01 to about 20 mg/cm$^2$, or from about 0.1 to about 10 mg/cm$^2$.

A method of reducing the severity of, reducing the number of, or preventing or forestalling the onset of, wrinkles or fine lines on human skin may comprise topically applying to an area of the skin in need thereof (e.g., wrinkled skin), an effective amount (e.g., 0.0001%-1% by weight, w/w) of a compound of Formulas I(a)-(d), alone or in combination with an effective amount (e.g., 0.01%-5% by weight, w/w) of retinol and/or an effective amount (e.g., 0.001%-5% by weight, w/w) of an alpha-hydroxy acid (e.g., glycolic acid) and/or a beta-hydroxy acid (e.g., salicylic acid).

It is also contemplated that the compositions of the invention will be useful for treating thin skin by topically applying the composition to thin skin of an individual in need thereof "Thin skin" is intended to include skin that is thinned due to chronological aging, menopause, or photo-damage and skin that is thinning prematurely. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in individuals that have not manifested signs of skin aging, most commonly in individuals under 25 years of age. The method may also reverse or treat signs of aging once manifested as is common in individuals over 25 years of age, or to slow the progression of dermatological aging in such individuals. The methods may be used to treat men and women. In some embodiments, the methods are employed to treat wrinkles in female skin, such as skin of the face.

It is also contemplated that the compositions of the invention will be useful for treating hyperpigmentation or otherwise unwanted pigmentation by topically applying the composition to skin of an individual in need thereof. The compositions may include one or more additional agents that combat pigmentation or hyperpigmentation, including tyrosinase inhibitors and/or melanosome transfer inhibitors. Special mention may be made of thiodipropionic acid and esters thereof (notably, di-lauryl esters); hydroquinone and the monobenzyl ether thereof; hydroquinone-beta-D-glucopyranoside; retinoids (e.g., retinoic acid); tretinoin; azelaic acid; Kojic acid (5-hydroxy-4-pyran-4-one-2-methyl); Mequinol (4-hydroxyanisole); Niacinamide; soy protein and other serine protease inhibitors; paper mulberry extract; Glabridin (licorice extract); *Arctostaphylos patula* and *Arctostaphylos viscida* extracts; Magnesium-L-ascorbyl-2-phosphate (MAP); 4-Isopropylcatechol; Aleosin; N-acetyl-4-S-cysteaminylphenol and N-propionyl-4-S-cysteaminylphenol; N-acetyl glucosamine; and Tranexamic acid (trans-4-aminomethylcyclohexanecarboxylic acid); to name a few.

In one embodiment, the compositions of the invention are applied to human skin to reduce sebum production or improve the appearance of skin affected by cellulite, and/or reduce unwanted lipogenesis or increase lipolysis. In this embodiment, the compounds of Formulas I(a)-I(d) can be formulated in cosmetically acceptable vehicles (as described herein) and may include one or more additional agents such as anti-acne ingredients (e.g., salicylic acid, benzoyl peroxide and other peroxides, sulfur, retinoids, etc.) in the case of a facial composition, or, in the case of a cellulite treatment, the formulation may comprise any ingredients suitable for treatment of cellulite, including without limitation, perilla oil and other unsaturated fatty oils and omega-3 fatty acids such as alpha-linolenic acid; caffeine; theophylline; xanthines; retinoids (e.g., retinol); and the like. A cellulite treatment according to the invention will typically be applied topically to skin suffering from cellulite, including skin of the buttocks and thighs for a period of time sufficient to improve the appearance thereof, including for example, daily treatment for at least four weeks, at least eight weeks, at least twelve weeks, or longer.

In another embodiment, the compounds of Formulas I(a)-I(d) are intended for oral use, including for pharmaceutical use. Pharmaceutical formulations will include pharmaceutically acceptable carriers (i.e., diluents and excipients). The pharmaceutical compositions may be included in solid dosage forms, including compressed tablets and capsules, or in liquid or powder forms. Pharmaceutical dosage forms will typically include from about 0.5 mg to about 200 mg, or from about 1 mg to about 100 mg of the compound of Formulas I(a)-I(d). The dosage forms may be immediate release, in which case they will typically comprise a water-soluble or dispersible carrier such as microcrystalline cellulose, mannitol, hydroxypropyl methyl cellulose, PVP or the like, or may be delayed, sustained, or modified release, in which case they may comprise water-insoluble polymers such as cellulose ethers (e.g., ethylcellulose), alone or in combination with water soluble or dispersible polymers, to regulate the rate of dissolution of the dosage form in the stomach.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, §201(i).

EXAMPLES

The following examples describe specific aspects of the invention to illustrate the invention but should not be construed as limiting the invention, as the examples merely provide specific methodology useful in the understanding and practice of the invention and its various aspects.

Example 1

Stimulation of Collagen and Hyaluronic Acid

Aryl-thiazole compounds of Formula I(c) and Formula I(d) were tested for the ability to stimulate collagen and hyaluronic acid.

Collagen. Human dermal fibroblasts (Cascade Biologics, Portland, Oreg.) were plated at in 96-well culture plates in supplemented medium (DMEM, 10% Fetal Bovine Serum, 1% Penicillin/Streptomycin and 1% L-Glutamine) overnight in humidified atmosphere of 10% $CO_2$ at 37° C. The following day, the medium was replaced with fresh medium (DMEM, 1% Penicillin/Streptomycin and 1% L-Glutamine) and the actives dissolved in a vehicle were added to the wells in triplicate. Vehicle was used as control. Following 48-hour incubation, the plates were removed from the incubator and the medium from each well was collected for the procollagen assay.

Collage production was measured using procollagen type I C-peptide (PIP) EIA kit (Takara Bio, Inc., Japan). Briefly, the conditioned medium was diluted 1:10 in Sample Diluent. 20 µl of diluted conditioned medium and 100 µl of antibody-POD conjugate solution were added to the wells of the Takara ELISA plate. The ELISA plate was incubated at 37° C. for 3 hours before the wells were washed four times with 400 µl of 1×PBS. At the end of wash, 100 µl of substrate solution (supplied with kit) was added to the wells and incubated at room temperature for 15 minutes. The reaction was stopped by adding 100 µl of 1N sulfuric acid to the wells. The absorbance was measured on a spectrophotometer at 450 nm wavelength. The amount of procollagen peptide in the conditioned medium was calculated from the standard curve. The stimulation of collagen production was shown as an increase in collagen over the control.

Hyaluronic Acid Assay Protocol

Human dermal fibroblasts (Cascade Biologics, Portland, Oreg.) were plated at in 96-well culture plates in supplemented medium (DMEM, 10% Fetal Bovine Serum, 1% Penicillin/Streptomycin and 1% L-Glutamine) overnight in humidified atmosphere of 10% $CO_2$ at 37° C. The following day, the medium was replaced with fresh medium (DMEM, 1% Penicillin/Streptomycin and 1% L-Glutamine) and the actives dissolved in a vehicle were added to the wells in triplicate. Vehicle was used as control. Following 48-hour incubation, the plates were removed from the incubator and the medium from each well was collected for the hyaluronic acid assay.

Hyaluronic acid production was measured using hyaluronic acid test kit (Corgenix, Inc. CO, USA). Briefly, 100 µl diluted conditioned medium was added to appropriate microwells and was incubated for 60 minutes at room temperature. After the incubation is complete, the conditioned medium was removed and 100 µl HRP-conjugated HABP solution was added to each well and incubated for 30 minutes at room temperature. Wash each well 4 times with PBS after the incubation is complete. Add 100 µl One-component Substrate Solution to each well and incubate for 30 minutes at room temperature. Add 100 µl Stopping Solution to stop the enzyme reaction and read the O.D. of each well at 450 nm. The amount of hyaluronic acid in the conditioned medium was calculated from the standard curve. The stimulation of hyaluronic acid production was shown as an increase in hyaluronic acid over the control.

Table 1 shows the percent collagen and hyaluronic acid stimulation following the above-described treatment with the aryl-thiazole compounds of Formula I(c) and Formula I(d). The "+" describes a stimulation of between 21-40%.

TABLE 1

Stimulation of collagen and hyaluronic acid.

| Compound | Concentration | Collagen stimulation | Hyaluronic acid stimulation |
| --- | --- | --- | --- |
| Formula I(c) | 0.0005% | + | — |
| Formula I(d) | 0.0005% | + | + |

As shown in Table 1, the aryl-thiazole compounds are potent stimulators of collagen and/or hyaluronic acid. It is believed that stimulation of collagen and hyaluronic acid leads to an improvement to the appearance of aging skin. The aryl-thiazole compounds of the invention are therefore contemplated to have beneficial effects on skin, including without limitation, reducing one or more signs of skin aging, and improving the aesthetic appearance of skin.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A cosmetic composition for improving the aesthetic appearance of human skin comprising a cosmetically acceptable vehicle, and an effective amount of a compound according to formula I(a):

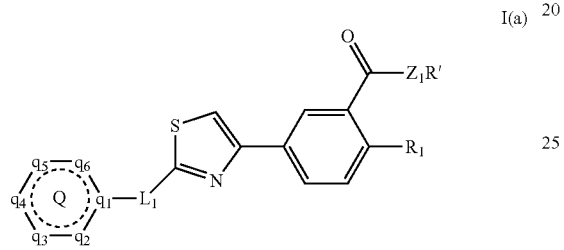

wherein, $Z_1$ is O or N(R");

$R_1$ is hydrogen or a group R;

$L_1$ is absent or is a radical of the form —$X^a$—$(CH_2)_n$—$(CH=CH)_m$—$X^b$—$(CH_2)_n$—$(CH=CH)_m$—$X^c$—, where $X^a$, $X^b$, and $X^c$ are independently a bond (i.e., absent), —O—, —S—, —NH—, —NR*— and "n" and "m" are independently at each occurrence integers from 0-2, with the proviso that $L_1$ comprises no more than four atoms in the direct chain between the thiazole ring and Q;

wherein, $q_1$ is N or C and is the point of attachment to $L_1$, and $q_2$-$q_6$ are independently selected from —N—, —NH—, —NR*—, —O—, —S—, —CH—, —CR—, —CR*—, and in the case where ring Q is a five membered ring, one of $q_2$-$q_6$ is a bond (i.e., it is absent), and where the dashed circle in ring Q indicates that the ring is aromatic, partially unsaturated, or saturated;

R is selected from hydrogen, —F; —Cl; —Br; —I; —OH, —OR*; —NH$_2$; —NHR*; —N(R*)$_2$; —N(R*)$_3^+$; N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)—N(R*)$_2$; —SH; —SR*; —CN; —NC; —(C=O)—R*; —CHO; —CO$_2$H; —CO$_2^-$; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —(C=NR)—O—R*; —O—(C=NR*)—R*, —SCN; —NCS; —NSO; —SSR*; —N(R*)—C(=O)—N(R*)$_2$; —N(R*)—C(=S)—N(R*)$_2$; —SO$_2$—R*; —O—S(=O)$_2$—R*; —S(=O)$_2$—OR*; —N(R*)—SO$_2$—R*; —SO$_2$—N(R*)$_2$; —O—SO$_3^-$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; C$_1$-C$_8$ perfluoroalkyl; an aliphatic C$_1$-C$_8$ hydrocarbon radical; a C$_1$-C$_8$ aromatic hydrocarbon radical; or a C$_1$-C$_8$ heteroaryl radical;

R* is independently at each occurrence hydrogen or a straight chained, branched, or cyclic C$_1$-C$_{10}$ hydrocarbon radical, which may be saturated, partially saturated, or aromatic, each of which may be optionally substituted with one or more groups R, or optionally substituted with 1-6 heteroatoms selected from nitrogen, oxygen, sulfur, or halogen;

R' and R" are independently selected from hydrogen, methyl, ethyl, butyl, propyl, pentyl, and hexyl, each of which may be optionally substituted with one or more groups R, or optionally substituted with 1-6 heteroatoms selected from nitrogen, oxygen, sulfur, or halogen; and wherein R' and R" may together from a 3-6 membered heterocycle;

and cosmetically acceptable salts thereof.

2. The composition according to claim 1, wherein $Z_1$ is N(R") and R' and R" are independently selected from hydrogen, methyl, ethyl, butyl, propyl, pentyl, and hexyl, and wherein R' and R" may together from a 3-6 membered heterocycle optionally substituted with 1-3 heteroatoms selected from nitrogen, oxygen, or sulfur; and $R_1$ is selected from hydrogen, halogen, hydroxyl, thiol, amino, alkylamino, diaklylamino, methyl, ethyl, methoxy, ethoxy; and wherein $L_1$ is a bond (i.e., it is absent) or $L_1$ is selected from —O—, —S—, —NR*—, —(CH$_2$)$_n$—, (CH$_2$)$_n$—O—, —O—(CH$_2$)$_n$—, —O—(CH$_2$)$_n$—O—, —(CH=CH)$_n$—, —(CH=CH)$_n$—O—, —O—(CH=CH)$_n$—, —O—(CH=CH)$_n$—O—, —(CH$_2$)$_n$—, —(CH$_2$)$_n$—S—, —S—(CH$_2$)$_n$—, —(CH=CH)$_n$—, —(CH=CH)$_n$—S—, —S—(CH=CH)$_n$—, —S—(CH=CH)$_n$—O—, —S—(CH=CH)$_n$—S—, —O—(CH=CH)$_n$—S—, —(CH$_2$)$_n$—NR*—, —NR*—(CH$_2$)$_n$—, —NR*—(CH$_2$)$_n$—O—, —NR*—(CH$_2$)$_n$—NR*—, —(CH=CH)$_n$—NR*—, —NR*—(CH=CH)$_n$—O—, —O—(CH=CH)$_n$—NR*—, —NR*—(CH=CH)$_n$—NR*—, —NR*—(CH$_2$)$_n$—S—, —S—(CH$_2$)$_n$—NR*—, —NR*—(CH=CH)$_n$—S—, —S—(CH=CH)$_n$—NR*—, —(CH$_2$)$_n$—O—(CH$_2$)$_n$—, —(CH$_2$)$_n$—S—(CH$_2$)$_n$—, —(CH$_2$)$_n$—NR*—(CH$_2$)$_n$—, herein "n" is independently at each occurrence an integer from 0-3.

3. The composition according to claim 1, wherein R' and R" are each hydrogen and $R_1$ is hydroxyl.

4. The composition according to claim 1, wherein $L_1$ is a bond or a group —(CH$_2$)$_n$—NR*—; and where Q has the form:

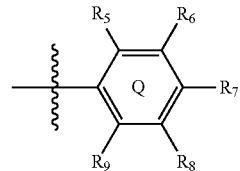

where $R_5$-$R_9$ are independently selected from hydrogen or R;

wherein at least one of $R_5$-$R_9$ is a group selected from hydroxyl, methoxy, ethoxy, amino, alkylamino, dialkylamino, thiol, thioether, cyano, methyl, ethyl, carboxyl, carbamyl, and nitro.

5. The composition according to claim 1, wherein $R_5$ is methoxy.

6. The composition according to claim 1, wherein $R_5$ and $R_6$ are methoxy.

7. The composition according to claim 1, wherein Q represents a five-membered heterocyclic ring selected from the following:

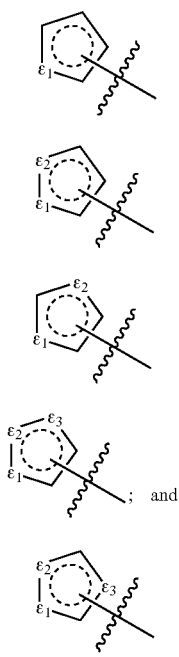

wherein $\epsilon_1$, $\epsilon_2$, and $\epsilon_3$, are independently selected from N, NH, NR*, S, and O; with the provision that where the point of attachment is $\epsilon_1$, $\epsilon_2$, or $\epsilon_3$, then that position represents N; and wherein carbon atoms which are not the point of attachment may be optionally substituted with a group R; and wherein the dashed circles indicate that each ring may comprise zero, one, or two double bonds.

8. The composition according to claim 4, wherein the compound has the structure of Formula I(b):

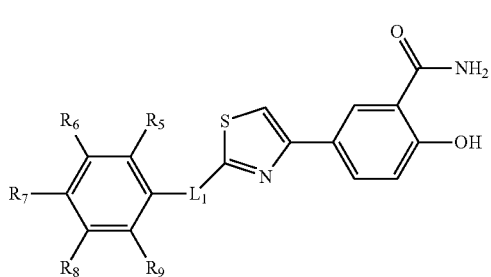

where $R_5$-$R_9$ are independently selected from hydrogen or R; $L_1$ is a bond (i.e., it is absent) or a group —O—, —S—, —NR*—, —(CH$_2$)$_n$—, —(CH$_2$)$_n$—O—, —O—(CH$_2$)$_n$—, —O—(CH$_2$)$_n$—O—, —(CH=CH)$_n$—, —(CH=CH)$_n$—O—, —O—(CH=CH)$_n$—, —O—(CH=CH)$_n$—O—, —(CH$_2$)$_n$—(CH=CH)$_n$—, —(CH=CH)$_n$—(CH$_2$)$_n$—, —(CH$_2$)$_n$—S—, —(CH=CH)$_n$—, —(CH=CH)$_n$—S—, —S—(CH=CH)$_n$—, —S—(CH=CH)$_n$—O—, —S—(CH=CH)$_n$—S—, —O—(CH=CH)$_n$—S—, —(CH$_2$)$_n$—NR*—, —NR*—(CH$_2$)$_n$—, —NR*—(CH$_2$)$_n$—O—, —NR*—(CH$_2$)$_n$—NR*—, —(CH=CH)$_n$—NR*—, —NR*—(CH=CH)$_n$—O—, —O—(CH=CH)$_n$—NR*—, —NR*—(CH=CH)$_n$—NR*—, —NR*—(CH$_2$)$_n$—S—, —S—(CH$_2$)$_n$—NR*—, —NR*—(CH=CH)$_n$—S—, —S—(CH=CH)$_n$—NR*—, —(CH$_2$)$_n$—O—(CH$_2$)$_n$—, —(CH$_2$)$_n$—S—(CH$_2$)$_n$—, oe —(CH$_2$)$_n$—NR*—(CH$_2$)$_n$—, wherein "n" is independently at each occurrence an integer from 0-3.

9. The composition according to claim 8, wherein at least one of $R_5$-$R_9$ is a group selected from halo, hydroxyl, methoxy, ethoxy, amino, alkylamino, dialkylamino, thiol, thioether, cyano, methyl, ethyl, carboxyl, carbamyl, methyl, trifluoromethyl, and nitro.

10. The composition according to claim 9, wherein $R_5$ is methoxy and $R_6$-$R_9$ are hydrogen.

11. The composition according to claim 9, wherein $R_5$ and $R_6$ are methoxy and $R_7$-$R_9$ are hydrogen.

12. The composition according to claim 8, wherein the compound has the structure of Formula I(c):

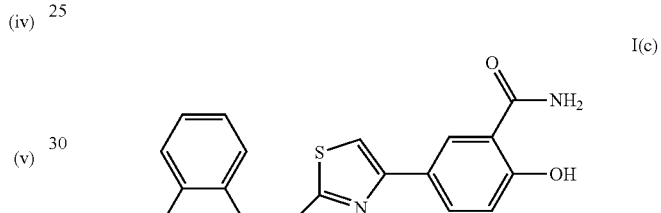

and cosmetically acceptable salts thereof.

13. The composition according to claim 8, wherein the compound has the structure of Formula I(d):

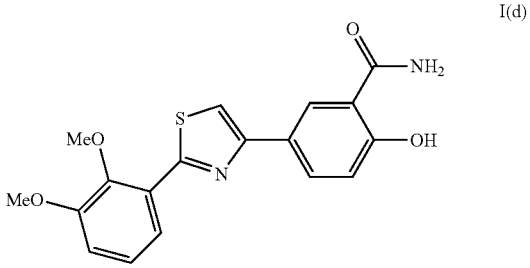 [SMILES: COc1cccc(-c2nc(-c3ccc(O)c(C(N)=O)c3)cs2)c1OC]

and cosmetically acceptable salts thereof.

14. The cosmetic composition according to claim 1, further comprising a cosmetic ingredient selected from a film forming polymer, a thickener, a pH adjuster, a preservative, an emulsifier, a gelling agent, an antioxidant, an emollient, a humectant, a fragrance, and a colorant.

15. The cosmetic composition according to claim 1, wherein said cosmetically acceptable vehicle comprises a water-in-oil, oil-in-water, silicone-in-water, or water-in-silicone emulsion and further comprises an emulsifier.

16. The cosmetic composition according to claim 1, wherein said effective amount comprises from about 0.00001% to about 1% by weight of said composition.

17. The composition according to claim 1, further comprising a retinoid selected from the group consisting of retinoic acid, retinol, retinal, retinyl acetate, and retinyl palmitate.

18. A method for improving the aesthetic appearance of human skin comprising topically applying to an area of the skin in need thereof a composition according to any of claim 1 for a time sufficient to improve the aesthetic appearance of said human skin, wherein said aesthetic improvement of said human skin is selected from the group consisting of:
- (a) treatment and/or reduction of fine lines or wrinkles;
- (b) reduction of skin pore size;
- (c) improvement in skin thickness, plumpness, and/or tautness;
- (d) improvement in skin smoothness, suppleness and/or softness;
- (e) improvement in skin tone, radiance, and/or clarity;
- (f) improvement in procollagen, and/or collagen production;
- (g) improvement in maintenance and remodeling of elastin;
- (h) improvement in skin texture and/or promotion of retexturization;
- (i) improvement in skin barrier repair and/or function;
- (j) improvement in appearance of skin contours;
- (k) restoration of skin luster and/or brightness;
- (l) replenishment of essential nutrients and/or constituents in the skin;
- (m) improvement of skin appearance decreased by aging and/or menopause;
- (n) improvement in skin moisturization;
- (o) increase in skin elasticity and/or resiliency;
- (p) treatment and/or reduction of skin sagging;
- (q) improvement in skin firmness; and
- (r) reduction of pigment spots and/or mottled skin; and
- (s) improvement of optical properties of skin by light diffraction or reflection.

19. The method according to claim 18, wherein said composition is applied at least once daily for a period of at least four weeks.

20. A method for treating wrinkles and fine lines in human skin comprising topically applying to an affected area of the skin a composition according to claim 1, for a time sufficient to improve the appearance of said wrinkles and fine lines.

* * * * *